United States Patent [19]

Daum

[11] 4,072,692
[45] Feb. 7, 1978

[54] TRANS-4-(8-HYDROXYOCTYL)-5-OCTYL-1,3-DITHIOLANE-2-THIONE

[75] Inventor: Sol Jacob Daum, Albany, N.Y.

[73] Assignee: Sterling Drug Inc., New York, N.Y.

[21] Appl. No.: 732,651

[22] Filed: Oct. 15, 1976

[51] Int. Cl.$^2$ .......................................... C07D 339/06
[52] U.S. Cl. .............................................. 260/327 M
[58] Field of Search .................................. 260/327 M

[56] References Cited

U.S. PATENT DOCUMENTS

| | | | |
|---|---|---|---|
| 3,445,480 | 5/1969 | Allais et al. | 260/327 |
| 3,978,225 | 8/1976 | Bender et al. | 424/276 |

*Primary Examiner*—Cecilia M. S. Jaisle
*Attorney, Agent, or Firm*—Thomas L. Johnson; B. Woodrow Wyatt

[57] ABSTRACT

Trans-4-(8-hydroxyoctyl)-5-octyl-1,3-dithiolane-2-thione, useful as a hypocholesteremic and hypotriglyceridemic agent, is prepared by treatment of the epoxide of oleyl alcohol with carbon disulfide and an alkali metal hydroxide in a lower-alkanol.

1 Claim, No Drawings

TRANS-4-(8-HYDROXYOCTYL)-5-OCTYL-1,3-DITHIOLANE-2-THIONE

BACKGROUND OF THE INVENTION a. Field of the Invention

This invention relates to a novel 2-thio-1,3-dithiolane compound and a method for its preparation.

b. Description of the Prior Art

The 1,3-dithiolane ring system is known (Ring Index, No. 138). Illustrative is the compound 4,5-dimethyl-1,3-dithiolane-2-thione, described by Iqbal and Owen, J. Chem. Soc. 1030 (1960); Overberger and Drucker, J. Org. Chem. 29, 360 (1964).

SUMMARY OF THE INVENTION

In its composition of matter aspect, the invention relates to a compound of the formula $$R-(CH_2)_7-\underset{S}{CH}\underset{\diagdown C \diagup}{\underset{\|}{\phantom{X}}}\underset{S}{CH}-(CH_2)_7CH_3 \qquad I$$

wherein R is $HOCH_2$.

In its process aspect the invention relates to a process for preparing the compound of formula I by reacting the epoxide to the formula $$R-(CH_2)_7-CH\underset{\diagdown O \diagup}{\phantom{XXX}}CH-(CH_2)_7CH_3 \qquad II$$

with carbon disulfide in the presence of an alkali metal hydroxide and a lower-alkanol.

DETAILED DESCRIPTION INCLUSIVE OF PREFERRED EMBODIMENTS

The epoxide of formula II is prepared by reacting oleyl alcohol (cis-9-octadecen-1-ol) with hydrogen peroxide or a peracid.

In order to prepare the compound of formula I, the epoxide of formula II is treated in the presence of an alkali metal hydroxide, preferably potassium or sodium hydroxide, and a lower-alkanol, preferably methanol or ethanol, with an excess of carbon disulfide. The reaction takes place readily at ambient temperature. The trans-isomer of the compound of formula I is preferentially formed.

Biological evaluation of the compound of the invention has shown that it possesss hypocholesteremic and hypotriglyceridemic activity and is therefore useful in treating atherosclerotic conditions brought about by elevated serum cholesterol and triglyceride levels. The hypocholesteremic and hypotriglyceridemic activity was measured by oral administration to rats according to methods of Turner et al., Scand. J. Clin. Lab. Investigation 9, 210 (1949); and Arnold et al., J. Atherosclerosis Research 7, 111-115 (1967).

EXAMPLE a. Epoxide of oleyl alcohol

Oleyl alcohol (125 g.) was added to a solution of 95 ml. of peracetic acid (40%) in 405 ml. of acetic acid containing 7.3 g. of sodium acetate. The reaction mixture was stirred for 3 hours and then added to 2 liters of water. The crystalline product which formed was collected by filtration, washed with water, dried and recrystallized from acetone to give 77.2 g. of oleyl alcohol epoxide, m.p. 48°-52° C.

b. 4-(8-Hydroxyoctyl)-5-octyl-1,3-dithiolane-2-thione (transisomer) [I; R is $HOCH_2$].

Carbon disulfide (50.5 ml.) was added to a solution of 39 g. of potassium hydroxide in 150 ml. of methanol cooled in an ice-bath. To this solution was added 75 g. of oleyl alcohol epoxide and the mixture was allowed to stand at room temperature for 5 days. The reaction mixture was diluted with water and heated on a steam bath under a ventilating hood for 1 hour to remove excess carbon disulfide and low-boiling sulfur compounds. The mixture was then acidified with hydrochloric acid and extracted with ether. The ether extracts were dried over anhydrous sodium sulfate and concentrated to remove the solvent. The residue crystallized and was triturated with a small amount of acetone and pentane to give 48.5 g. of 4-(8-hydroxyoctyl)-5-octyl-1,3-dithiolane-2-thione (trans-isomer), m.p. 40°-47° C. in the form of yellow plates.

When administered orally to rats at a dose level of 192 mg/kg, 4-(8-hydroxyoctyl)-5-octyl-1,3-dithiolane-2-thione (trans-isomer) reduced the serum cholesterol and triglycerides by 22% and 50%, respectively.

I claim:

1. The trans-isomer of 4-(8-hydroxyoctyl)-5-octyl-1,3-dithiolane-2-thione.